(12) United States Patent
Ayene et al.

(10) Patent No.: US 9,522,164 B2
(45) Date of Patent: Dec. 20, 2016

(54) DISULFIDE CHEMOTHERAPEUTIC AGENTS AND METHODS OF USE THEREOF

(71) Applicant: Lankenau Institute for Medical Research, Wynnewood, PA (US)

(72) Inventors: Iraimoudi S. Ayene, Newtown Square, PA (US); George C. Prendergast, Penn Valley, PA (US)

(73) Assignee: LANKENAU INSTITUTE FOR MEDICAL RESEARCH, Wynnewood, PA (US)

( * ) Notice: Subject to any disclaimer, the term of this patent is extended or adjusted under 35 U.S.C. 154(b) by 0 days.

(21) Appl. No.: 14/084,064

(22) Filed: Nov. 19, 2013

(65) Prior Publication Data

US 2014/0079812 A1 Mar. 20, 2014

Related U.S. Application Data

(62) Division of application No. 12/743,682, filed as application No. PCT/US2008/083994 on Nov. 19, 2008, now Pat. No. 8,586,636.

(60) Provisional application No. 60/989,383, filed on Nov. 20, 2007.

(51) Int. Cl.

| | |
|---|---|
| A61K 31/10 | (2006.01) |
| A61K 31/198 | (2006.01) |
| A61K 33/24 | (2006.01) |
| A61K 9/00 | (2006.01) |
| A61K 31/194 | (2006.01) |
| A61K 45/06 | (2006.01) |
| A61K 31/7048 | (2006.01) |

(52) U.S. Cl.
CPC ............ *A61K 33/24* (2013.01); *A61K 9/0019* (2013.01); *A61K 31/10* (2013.01); *A61K 31/194* (2013.01); *A61K 31/198* (2013.01); *A61K 31/7048* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,919,816 | A | * | 7/1999 | Hausheer et al. ............ 514/449 |
| 6,037,336 | A | | 3/2000 | Hausheer et al. |
| 6,312,734 | B1 | * | 11/2001 | Kozhemyakin et al. ..... 424/617 |
| 6,504,049 | B1 | | 1/2003 | Kochat |
| 6,552,060 | B1 | | 4/2003 | Kirkpatrick |
| 6,596,320 | B1 | | 7/2003 | Hausheer |
| 7,169,412 | B2 | | 1/2007 | Kozhemyakin et al. |
| 2002/0044978 | A1 | | 4/2002 | Cheon et al. |
| 2003/0133994 | A1 | | 7/2003 | Hausheer et al. |
| 2003/0211514 | A1 | | 11/2003 | Penninger et al. |
| 2004/0116496 | A1 | | 6/2004 | Kirkpatrick et al. |

FOREIGN PATENT DOCUMENTS

| | | |
|---|---|---|
| EP | 0 656 360 A1 | 6/1995 |
| WO | 99/20264 | 4/1999 |
| WO | 01/62259 | 8/2001 |
| WO | 03092675 | 11/2003 |
| WO | 2005/007108 | 1/2005 |
| WO | 2007/041546 | 4/2007 |
| WO | 2007/109184 A2 | 9/2007 |

OTHER PUBLICATIONS

Chiba, T. Yakugaku Zasshi, 1969, vol. 89, No. 2, pp. 241-247.*
Gandara et al. Seminars in Oncology, Feb. 2002, vol. 29, No. 1, supplement 4, pp. 102-109.*
Sharan, R.N., et al. "2-Mercaptopropionylglycine affords enhanced radioprotection after a liposome encapsulation." J Radiat Res (Tokyo). Mar. 1995;36(1):31-7.
Biaglow, J.E., et al. "Radiation response of cells during altered protein thiol redox." Radiat Res. Apr. 2003;159(4):484-94.
Biaglow, J.E., et al. "Role of vicinal protein thiols in radiation and cytotoxic responses." Radiat Res. Mar. 2006;165(3):307-17.
Ayene, I.S., et al. "Mutation in G6PD gene leads to loss of cellular control of protein glutathionylation: mechanism and implication." J Cell Biochem. Jan. 1, 2008;103(1):123-35.
Ayene, I.S., et al. "Oxidation of cellular thiols by hydroxyethyldisulphide inhibits DNA double-strand-break rejoining in G6PD deficient mammalian cells." Int J Radiat Biol. Nov. 2000;76(11):1523-31.
Townsend, D.M., et al. "NOV-002, a glutathione disulfide mimetic, as a modulator of cellular redox balance." Cancer Res. Apr. 15, 2008;68(8):2870-7.
Sittadjody, S., et al. "Cell-secific redox pathways can be targeted using disulfides to induce cell death: Enhancement by low pH and quercetin." Proceedings of the American Association for Cancer Research Annual. Apr. 2007;48:559-560, #2356.
Reinhart, F.E., et al. "The anti-tumor activities in vitro of 5-imino-1,2,4-dithiazolidin-3-thione and bis (diethylthiocarbamoyl) disulfide toward the krebs-2 ascites carcinoma." Journal of the Franklin Institute. Jan. 1958;265(1):58-62.
Lee, Y.J., et al. "Enhancement of metabolic oxidative stress-induced cytotoxicity by the thioredoxin inhibitor 1-methylpropyl 2-imidazolyl disulfide is mediated through the ASK1-SEK1-JNK1 pathway." Mol Pharmacol. Dec. 2002;62(6):1409-17.
Yokomizo, A., et al. "Cellular levels of thioredoxin associated with drug sensitivity to cisplatin, mitomycin C, doxorubicin, and etoposide." Cancer Res. Oct. 1, 1995;55(19):4293-6.
Wouters, A., et al. "Review: implications of in vitro research on the effect of radiotherapy and chemotherapy under hypoxic conditions." Oncologist. Jun. 2007;12(6):690-712.

(Continued)

*Primary Examiner* — James D Anderson
(74) *Attorney, Agent, or Firm* — Robert C. Netter, Jr.; Dann, Dorfman, Herrell & Skillman

(57) ABSTRACT

Compositions and methods for the treatment of cancer are provided.

10 Claims, 18 Drawing Sheets

(56) References Cited

OTHER PUBLICATIONS

Boven, E., et al. "Phase I and pharmacokinetic study of the novel chemoprotector BNP7787 in combination with cisplatin and attempt to eliminate the hydration schedule." Br J Cancer. May 9, 2005;92(9):1636-43.

Fuchs et al., 2-Mercaptopropionylglycine and related compounds in treatment of mitochondrial dysfunction and postischemic myocardial damage, Arzneimittelforschung,1985, 1394-1402, 35(9). (Abstract only).

Veit et al., Uncoupler- and hypoxia-induced damage in the working rat heart and its treatment, I.Observations with uncouplers of oxidative phosphorylation, Basic Research in Cardiology, 1985, 107-115, 80.

Fuchs et al., Uncoupler- and hypoxia-induced damage in the working rat heart and its treatment, II. Hypoxic reduction of aortic flow and its reversal, Basic Research in Cardiology, 1985, 231-240, 80.

Iciek, M., et al., "Selective Effects of Diallyl Disulfide, a Sulfane Sulfur Precursor, in the Liver and Ehrlich Ascites Tumor Cells", Eur. J. Pharmacol. (2007) 569:1-7.

Dwivedi, C., et al., "Chemoprevention of Chemically Induced Skin Tumor Development by Diallyl Sulfide and Diallyl Disulfide", Pharm. Res. (1992) 9:1668-1670.

\* cited by examiner

DISULFIDE CHEMOTHERAPEUTIC AGENTS AND METHODS OF USE THEREOF

This application is a divisional application of U.S. patent application Ser. No. 12/743,682, filed Jul. 27, 2010, now U.S. Pat. No. 8,586,636, which is a §371 application of PCT/US2008/083994, filed Nov. 19, 2008, which claims priority under 35 U.S.C. §119(e) to U.S. Provisional Patent Application No. 60/989,383, filed on Nov. 20, 2007. Each of the foregoing applications is incorporated by reference herein.

Pursuant to 35 U.S.C. §202(c) it is acknowledged that the U.S. Government has certain rights in the invention described, which was made in part with funds from the National Institutes of Health, Grant Number CA109604.

FIELD OF THE INVENTION

The present invention relates to disulfide chemotherapeutic agents and methods of use thereof.

BACKGROUND OF THE INVENTION

Several publications and patent documents are cited throughout the specification in order to describe the state of the art to which this invention pertains. Each of these citations is incorporated herein by reference as though set forth in full.

Radiation and chemotherapeutic agents are effective in the treatment of cancer in humans, particularly solid tumors. However, cancer cells that survive the initial treatment become resistant to subsequent treatment. This resistance to subsequent treatment is a major reason for the lack of better overall survival of these patients. Hypoxia is also known to play a major role in the outcome of cancer therapy. A vast majority of human solid tumors exhibit hypoxia. Unfortunately, hypoxic tumor cells are more resistant than normoxic tumor cells to radiation treatment and chemotherapy and these hypoxic cells are considered a significant contributor to disease relapse (see, e.g., Teicher et al. (1990) Cancer Res., 50:3339-3344; Grau and Overgaard (1988) Radiother. Oncol. 13:301-309). Several studies have demonstrated that the hypoxic cells of solid tumors also lack glucose.

Glucose deprived cancer cells that consist of both hypoxic and normoxic cancer cells are more resistant to chemotherapeutic agents (Cui et al. (2007) Cancer Res., 67:3345-55). Glucose depletion is common in most solid tumors due to higher metabolic activity and lack of perfusion due to disorganized vasculature. It is also believed to induce tolerance to stress. There is a recent upsurge of interest by several labs in understanding the impact of glucose deprivation on cancer cells since the overall steady state level of glucose is believed to be lower in solid tumors particularly in hypoxic tumors (Aronen et al. (2000) Clin. Cancer Res., 6:2189-200; Rajendran et al. (2004) Clin. Cancer Res., 10:2245-52; Schroeder et al. (2005) Cancer Res., 65:5163-71). It has been suggested that the decrease in glucose level may be due to higher metabolic activity of cancer cells (Schroeder et al. (2005) Cancer Res., 65:5163-71). Ischemic conditions caused by disorganized vasculature may also be responsible for the lower level of glucose in solid tumors (Schroeder et al. (2005) Cancer Res., 65:5163-71). Several recent studies have looked into the impact of glucose deprivation on cancer cells in vitro (Yun et al. (2005) J. Biol. Chem., 280: 9963-9972; Katol et al. (2002) Oncogene, 21: 6082-6090; Ryoo et al. (2006) Biol. Pharm. Bull., 29:817-820). These studies have indicated several molecular mechanisms may be involved in the survival of glucose deprived tumor cells. These studies have demonstrated the importance of targeting glucose depleted cancer cells since it induces survival molecules that enable them to survive and be less responsive to therapy in spite of lack of glucose.

Glucose-6-phosphate dehydrogenase (G6PD) is the first and rate-limiting enzyme of the oxidative pentose phosphate cycle (OPPC). Glucose, a substrate for the OPPC, is required for OPPC mediated detoxification of oxidants/disulfides. Glucose is utilized as a substrate by oxidative pentose phosphate cycle to generate reductants. These reductants are utilized to maintain reduced glutathione homeostasis in mammalian cells when exposed to oxidants/disulfides. Glutathione is a tripeptide consisting of glycine, cysteine and glutamate. The reduced GSH is up to 100 folds higher than the oxidized GSH (GSSG) in mammalian cells under normal conditions. However, the oxidized GSH produced by oxidants/disulfides is detrimental to cancer cells.

SUMMARY OF THE INVENTION

In accordance with one aspect of the instant invention, methods of treating cancer in a patient in need thereof are provided. In one embodiment, the method comprises administering a composition comprising at least one disulfide containing compound and a pharmaceutically acceptable carrier. The disulfide containing compound may be selected from the group consisting of hydroxyethyldisulfide (HEDS), disulfide of mercaptopropionylglycine (MPG) (glycinepropionyldisulfide), disulfide of MPG and ME, disulfide of 2-sulfanylethanesulfonate (mesna), disulfide of MPG and mesna, and disulfide of ME and mesna. In another embodiment, the cancer cells are hypoxic, normoxic, glucose deprived, glucose normal, and/or resistant to radiation and/or chemotherapeutic agents.

According to another aspect, methods of treating cancer in a patient in need thereof are provided wherein the cancer comprises hypoxic cancer cells. In one embodiment, the method comprises the administration of at least one disulfide containing compound and, optionally, the administration of at least one chemotherapeutic agent, hypoxic toxin and/or radiation. In a particular embodiment, the chemotherapeutic agent is selected from the group consisting of a topoisomerase II inhibitor and a platinum complex. In another embodiment, the hypoxic toxin is selected from the group consisting of tirapazamine, AQ4N, 5-nitroimidazole, nimorazole, etanidazole, mitomycin C analog E09, 2-nitroimidazole CI-1010, and other hypoxic specific bioreductive drugs. In yet another embodiment, the disulfide containing compound is administrated sequentially and/or concurrently with the at least one chemotherapeutic agent, hypoxic agent, and/or radiation.

According to another aspect, methods of treating cancer in a patient in need thereof are provided wherein the cancer comprises glucose deprived normoxic cancer cells. In one embodiment, the method comprises the administration of at least one disulfide containing compound and, optionally, the administration of at least one chemotherapeutic agent and/or radiation. In a particular embodiment, the chemotherapeutic agent is selected from the group consisting of a topoisomerase II inhibitor and a platinum complex. In yet another embodiment, the disulfide containing compound is administrated sequentially and/or concurrently with the at least one chemotherapeutic agent and/or radiation.

Methods of treating cancer in a patient in need thereof are also provided wherein the cancer comprises normoxic cancer cells with normal glucose. In one embodiment, the method comprises the administration of the administration of at least one disulfide containing compound and, optionally, at least one inhibitor of glucose-6-phosphate dehydrogenase (G6PD) and/or at least one chemotherapeutic agent, hypoxic toxin, and/or radiation. The inhibitor of G6PD may be selected from the group consisting of dehydroepiandrosterone (DHEA), DHEA-sulfate, 2-deoxyglucose, halogenated DHEA, epiandrosterone, isoflurane, sevoflurane, diazepam, and G6PD targeted siRNA/shRNA molecules.

According to another aspect of the instant invention, compositions for the treatment of cancer are provided. In a particular embodiment the composition comprises at least one disulfide containing compound and at least one pharmaceutically acceptable carrier. In a particular embodiment, the composition further comprises at least one chemotherapeutic agent. In another embodiment the composition comprises at least one disulfide containing compound, at least one hypoxic toxin, and at least one pharmaceutically acceptable carrier. The composition may further comprise at least one inhibitor of glucose-6-phosphate dehydrogenase (G6PD). In a particular embodiment, the composition comprises a disulfide of MPG, at least one pharmaceutically acceptable carrier, and, optionally, at least one other disulfide containing compound.

DETAILED DESCRIPTION OF THE INVENTION

Figure 1:
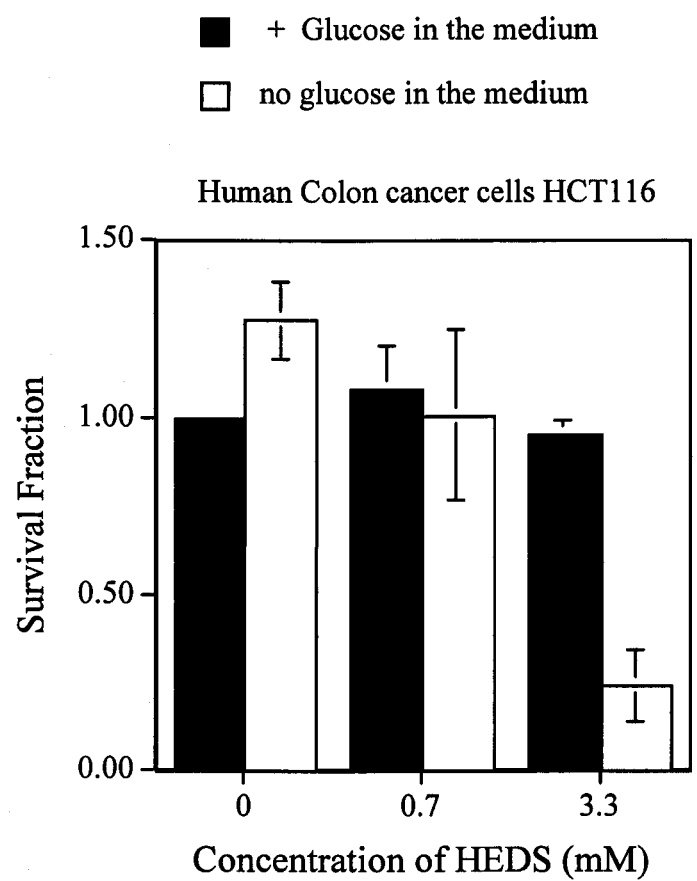
FIG. 1 is a graph depicting the survival of radiation sensitive human colon cancer cells in the presence or absence of glucose and various amounts of HEDS.

As described hereinbelow, it has been determined that radiation resistant p53 mutant HT29 colon cancer cells become more resistant to radiation when deprived of glucose. This raises the importance of identifying agents that can target glucose deprived cancer cells. In accordance with the instant invention, it has been determined that oxidants/disulfides that are specific for oxidative pentose phosphate cycle deficient cells can be used to target various types of cancer cells in solid tumors such as hypoxic cancer cells, glucose deprived cancer cells, normoxic cancer cells, and glucose containing cancer cells. This approach improves the efficacy of radiation and chemotherapeutic agents since it targets all glucose deprived cancer cells, which comprises of both hypoxic and non hypoxic cancer cells. In accordance with the instant invention, novel oxidants are also provided which are specific for glucose deprived hypoxic and non hypoxic cells and oxidative pentose cycle deficient cancer cells. Indeed, the lack of glucose mediated intracellular metabolic activity results in the intracellular accumulation of one such oxidant/disulfide, which caused oxidative stress via GSH depletion leading to cell death, and improvement in human cancer cells response to radiation and chemotherapeutic agents.

In accordance with the instant invention, methods for treating cancer are provided. The methods comprise the administration of at least one disulfide containing compound to a patient in need thereof. In one embodiment, the disulfide containing compound is administered to hypoxic cancer cells and/or glucose deprived cancer cells, optionally, in combination with at least one chemotherapeutic agent, hypoxic toxin and/or radiation (e.g., ionizing radiation). In a particular embodiment, the chemotherapeutic agent(s) comprise at least one topoisomerase II inhibitor and/or a platinum complex. In another embodiment, the hypoxic toxin(s) comprise at least one from the group consisting of tirapazamine, AQ4N, 5-nitroimidazole, nimorazole, etanidazole, mitomycin C analog E09, 2-nitroimidazole CI-1010, and other hypoxic specific bioreductive drugs. The disulfide containing compound can be administrated sequentially (e.g., prior to or after) and/or concurrently with the at least one chemotherapeutic, hypoxic toxin, agent and/or radiation.

In another embodiment, normoxic cancer cells can be sensitized to at least one chemotherapeutic agent and/or radiation by the administration of at least one inhibitor of glucose-6-phosphate dehydrogenase (G6PD) and at least one disulfide containing compound. Accordingly, the instant invention encompasses methods of treating cancer in a patient in need thereof, wherein the cancer comprises normoxic cells and the method comprises the administration of at least one G6PD inhibitor and at least one disulfide containing compound, optionally, prior to, and/or concurrently with, at least one chemotherapeutic agent and/or radiation. In a particular embodiment, the chemotherapeutic agent(s) comprise at least one topoisomerase II inhibitor and/or a platinum complex.

Disulfide containing compounds are readily available (see, e.g., Sigma Aldrich 2006-2007 catalog). In one embodiment, the disulfide containing compounds are di-alkyl disulfides (e.g., disulfides of lower alkyls comprising at least one sulfur atom) or di-aryl disulfides, wherein the members of the disulfide can be the same (symmetrical disulfide) or different (asymmetrical disulfide). In another embodiment, the disulfide containing compounds are disulfides comprising thiamine, such as, without limitation, thiamine disulfide, thiamine propyl disulfide, and thiamine tetrahydrofuryl disulfide. In another embodiment, exemplary disulfide containing compounds include, without limitation, hydroxyethyldisulfide (HEDS; a disulfide of mercaptoethanol (ME)), disulfide of mercaptopropionylglycine (MPG), disulfide of MPG and a lower alkyl, disulfide of MPG and ME, disulfide of mesna (2-sulfanylethanesulfonate), disulfide of MPG and mesna, and disulfide of ME and mesna. In a particular embodiment, the disulfide containing compound is a disulfide of MPG.

The instant invention also encompasses compositions comprising at least one agent described hereinabove (e.g., disulfide containing compound(s), G6PD inhibitor(s), chemotherapeutic agent(s), hypoxic toxin etc.) and at least one pharmaceutically acceptable carrier. In a particular embodiment, the compositions of the instant invention can be administered to a patient, in need thereof, for the treatment or prevention of cancer.

Cancers that may be treated using the present protocols include, but are not limited to: prostate cancers, colorectum, colon, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In a particular embodiment, the cancer is a solid tumor.

Inhibitors of glucose-6-phosphate dehydrogenase (G6PD) include, without limitation, dehydroepiandrosterone (DHEA), DHEA-sulfate, 2-deoxyglucose, halogenated DHEA, epiandrosterone, isoflurane, sevoflurane, diazepam, and siRNA/shRNA molecules (see, e.g., (Park et al. (2005) Mol. Cell Biol., 25:5146-57; Ho et al. (2006) Cytometry Part A, 69A:1054-1061; WO/2006/083051; WO/2007/117048; Lamberton et al. (2003) Mol. Biotech. 24:111-119; Invitrogen (Carlsbad, Calif.); Santa Cruz Biotechnologies (Santa Cruz, Calif.); and OriGene Technologies (Rockville, Md.)).

Definitions

The term "alkyl," as employed herein, includes straight, branched, and cyclic chain hydrocarbons containing about 1 to 20 carbons, particularly about 1 to 10 carbons, and more particularly about 1 to 5 carbons (i.e., a lower alkyl). The hydrocarbon chain of the alkyl groups may be interrupted with one or more oxygen, nitrogen, or sulfur atoms (particularly 1 to about 3 heteroatoms, more particularly one heteroatom) and may be unsaturated (contain one or more double or triple bonds). The alkyl group may optionally be substituted (e.g., with halo, alkyl, haloalkyl, alkoxyl, alkylthio, hydroxy, methoxy, carboxyl, oxo, epoxy, alkyloxycarbonyl, alkylcarbonyloxy, amino, carbamoyl, urea, alkylurea, aryl, ether, ester, thioester, nitrile, nitro, amide, carbonyl, carboxylate, sulfonate, and thiol). In a preferred embodiment, the alkyl of the instant invention comprises at least one sulfur atom.

The term "aryl," as employed herein, refers to monocyclic and bicyclic aromatic groups containing about 6 to 10 carbons in the ring portion. Aryl groups may be optionally substituted through available carbon atoms. The aromatic groups may be a heteroaryl (a ring system that includes at least one sulfur, oxygen, or nitrogen heteroatom ring members).

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein, the term "hypoxic" refers to a lower level of oxygen or oxygen tension in a cell or tissue compared to a normal cell or tissue. Cells or tissues are hypoxic when the $O_2$ concentration is lower than the normal level of oxygen in these particular cells or tissues. The term "hypoxic tumor cells" or "hypoxic cancer cells" refers to tumor cells or tissues having lower levels of oxygen or oxygen tension than the corresponding normal cells or tissues. As used herein, the term "normoxic" refers to an oxygen concentration that is normal for the cell and/or tissue of interest.

As used herein, the term "glucose deprived" refers to a lower level of glucose in a cell or tissue compared to a normal cell or tissue. Cells or tissues are glucose deprived when the glucose concentration is lower than the normal level of glucose in these particular cells or tissues. The term "glucose deprived cancer cells" refers to tumor cells or tissues having lower levels of glucose than the corresponding normal cells or tissues. As used herein, the term "normal glucose" refers to a glucose concentration that is normal for the cell and/or tissue of interest.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas* exotoxin, and others listed above); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes; bioreductive alkylators such as mitomycin, procarbazine, dacarbazine and altretamine); DNA strand-breakage agents (e.g., bleomycin); topoisomerase II inhibitors; DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); indoleamine 2,3-dioxygenase inhibitors (e.g., 1-methyl-tryptophan); and antihormonal antigens (e.g., tamoxifen, antiandrogen agents such as flutamide; and antiadrenal agents such as mitotane and aminoglutethimide). Platinum complexes include, without limitation, cisplatin (cis-diamine-dichloroplatinum (II)), carboplatin (diammine(1,1-cyclobutanedicarboxylato)-platinum(II)), tetraplatin (ormaplatin; tetrachloro(1,2-cyclohexanediamine-N,N')-platinum(IV)), thioplatin (bis(O-ethyldithiocarbonato)platinum(II)), satraplatin, nedaplatin, oxaliplatin, heptaplatin, iproplatin, transplatin, lobaplatin, cis-aminedichloro(2-methylpyridine)platinum, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)), JM335 (trans-amminedichloro(cyclohexylamine)dihydroxoplatinum(IV)), and (trans,trans,trans)bis-mu-(hexane-1,6-diamine)-mu-[diamine-platinum(II)]bis[diamine(chloro)platinum(II)]tetrachloride. Topoisomerase II inhibitors include, without limitation, amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide (VM-26).

The term "ionizing radiation" refers to radiation conventionally employed in the treatment of tumors. The radiation, administered either as a large single dosage or as repeated smaller dosages, typically initiates ionization of water thereby forming reactive oxygen species. Ionizing radiation includes, without limitation, x-rays, electron beams, gamma rays, and the like. As used herein, the term "high dose radiation" refers to any dose over 0.5 Gy or any dose that might be used therapeutically to kill cells.

"Hypoxic toxins" include, without limitation, tirapazamine, AQ4N, 5-nitroimidazole, nimorazole, etanidazole, mitomycin C analog E09, 2-nitroimidazole CI-1010, and other hypoxic specific bioreductive drugs.

The term "sensitize", as used herein, refers to the ability of an agent to increase the sensitivity of cells (e.g., tumor cells) to chemotherapeutic agents and/or radiation. Radiosensitizers increase the sensitivity of cancerous cells to the toxic effects of radiation.

Therapeutics

The compounds to be administered to a patient in accordance with the methods of the instant invention may, where suitable, be incorporated into a single pharmaceutical composition. Alternatively, the individual compounds may be incorporated into separate pharmaceutical compositions for the administration to a patient, which may then be contained within a kit. In another embodiment, the components of the pharmaceutical compositions are different from each other (e.g., the disulfide containing compound is a different compound than the chemotherapeutic agent).

The pharmaceutical compositions of the instant invention may comprise a pharmaceutically acceptable carrier suitable for the delivery of the inhibitors by any route of administration such as, without limitation, topically, orally, rectally, by injection, intravenously, intramuscularly, intraperitoneally, or by direct administration/injection to the tumor and/or surrounding area.

The dose and dosage regimen of a pharmaceutical preparation may be determined by a physician considering the patient's age, sex, weight, general medical condition, and the specific condition and severity thereof for which the preparation is being administered. The physician may also consider the route of administration of the agent, the pharmaceutical carrier with which the agent may be combined, and the biological activity of the agent(s).

The examples set forth below are provided to better illustrate certain embodiments of the invention. They are not intended to limit the invention in any way.

EXAMPLE I

Disulfides of the instant invention such as MPG disulfide may be synthesized by methods described in Hunter et al. (2006) J. Org. Chem., 71:8268-8271; Bao and Shimizu (2003) Tetrahedron, 59:9655-9659; Sanz et al. (2002) Synthesis 856-858; and the like. Briefly, symmetrical disulfides may be synthesized by the conversion of mono thiols to disulfides in the presence of dimethyl sulfoxide catalyzed by dichlorodioxomolybdenum(VI). Unsymmetrical disulfide may be synthesized by conversion of two different mono thiols into unsymmetrical disulfide in the presence of 1-chlorobenzotriazole.

EXAMPLE II

Glucose depletion is common in most solid tumors due to higher metabolic activity and lack of perfusion due to disorganized vasculature. Glucose depletion is believed to induce tolerance to stress and therapy. Glucose deprivation induces radiation resistance in already radiation resistant p53 mutant cancer cells.

The use of HEDS, an oxidant/disulfide, to increase the response of radiation sensitive and radiation resistant human colon cancer cells to γ radiation was investigated. In glucose containing medium, cancer cells showed HEDS concentration dependent increase in detoxification of HEDS to mercaptoethanol (ME). The depletion of intracellular glucose as a result of glucose depletion in the medium resulted in the inability of these cancer cells to detoxify HEDS into ME. Further, HEDS decreased the glutathione (GSH) level in glucose deprived cancer cells.

Figure 2:
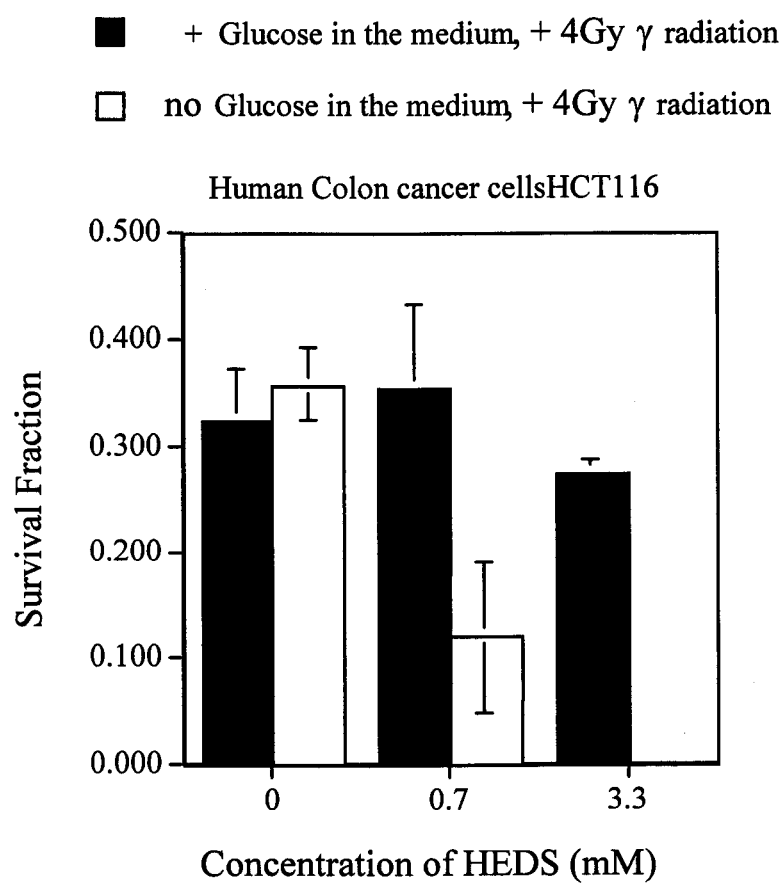
FIG. 2 is a graph depicting the survival of radiation sensitive human colon cancer cells exposed to 4Gy γ irradiation in the presence or absence of glucose and various amounts of HEDS.
Figure 3:
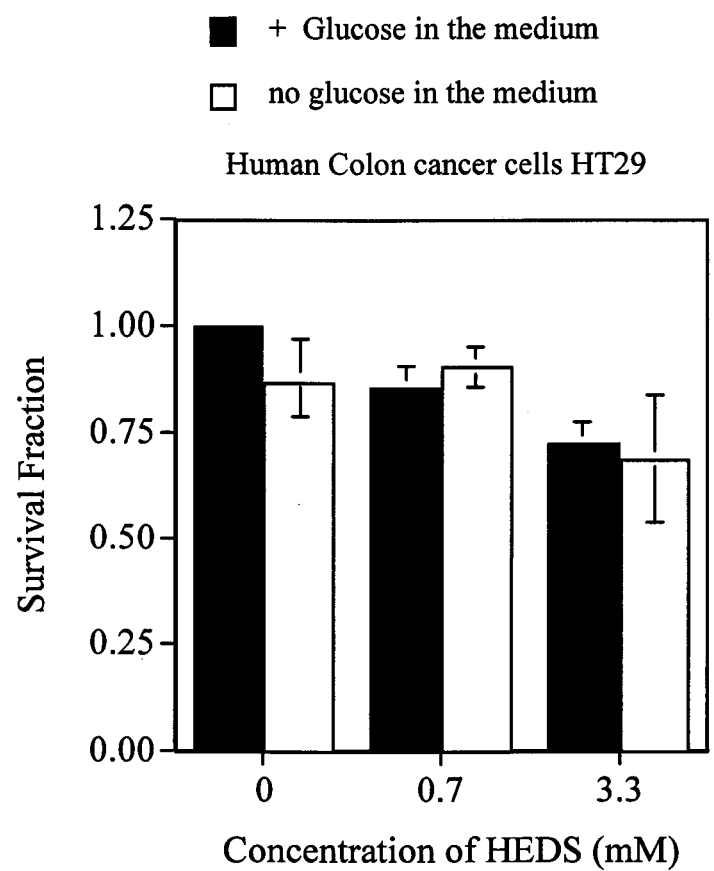
FIG. 3 is a graph depicting the survival of radiation resistant human colon cancer cells in the presence or absence of glucose and various amounts of HEDS.

FIGS. 1, 2, 3 and 4 demonstrate that HEDS in combination with radiation significantly decreased the survival of radiation sensitive (HCT116) and radiation resistant (HT29) human colon cancer cells. The clonogenic assay show that HEDS alone has little/no cytotoxic effects on these cells in the presence of glucose (FIGS. 1 and 3). In the absence of glucose, higher concentration of HEDS alone decreased the survival of HCT116 by 75% but with no significant effect on the radiation resistant HT29 cells (FIGS. 1 and 3). The combined treatment with HEDS and radiation showed HEDS mediated sensitization of both radiation sensitive (FIG. 2) and resistant (FIG. 4) cancer cells to radiation in the absence of glucose.

In FIG. 1, radiation sensitive human colon cancer cells HCT116 were deprived of glucose for 4 hours and then treated with various concentrations of HEDS for 3 hours. The cells were washed and replenished with fresh growth medium. Colony assays were carried out by plating cells at concentration that gives no more than 200 colonies. Each experiment was repeated at least three times with errors as shown unless smaller than points plotted.

For FIG. 2, HCT116 cells were deprived of glucose for 4 hours, treated with various concentrations of HEDS for 1 hour, and then exposed to 4 Gy irradiation. Two hours after irradiation, the cells were washed and replenished with fresh growth medium. The colony assay was then performed as described above for FIG. 1.

For FIG. 3, radiation resistant human colon cancer cells HT29 were deprived of glucose for 4 hours and then treated with various concentrations of HEDS for 3 hours. The cells were washed and replenished with fresh growth medium. For FIG. 4, HT29 cells were deprived of glucose for 4 hours, treated with various concentrations of HEDS, and then treated for 1 hour before 4 Gy irradiation. Two hours after irradiation, the cells were washed and replenished with fresh growth medium. Colony assays were carried out by plating cells at concentration that gives no more than 200 colonies. Each experiment was repeated at least three times with errors as shown unless smaller than points plotted. The cells were washed and replenished with fresh growth medium.

Figure 4:
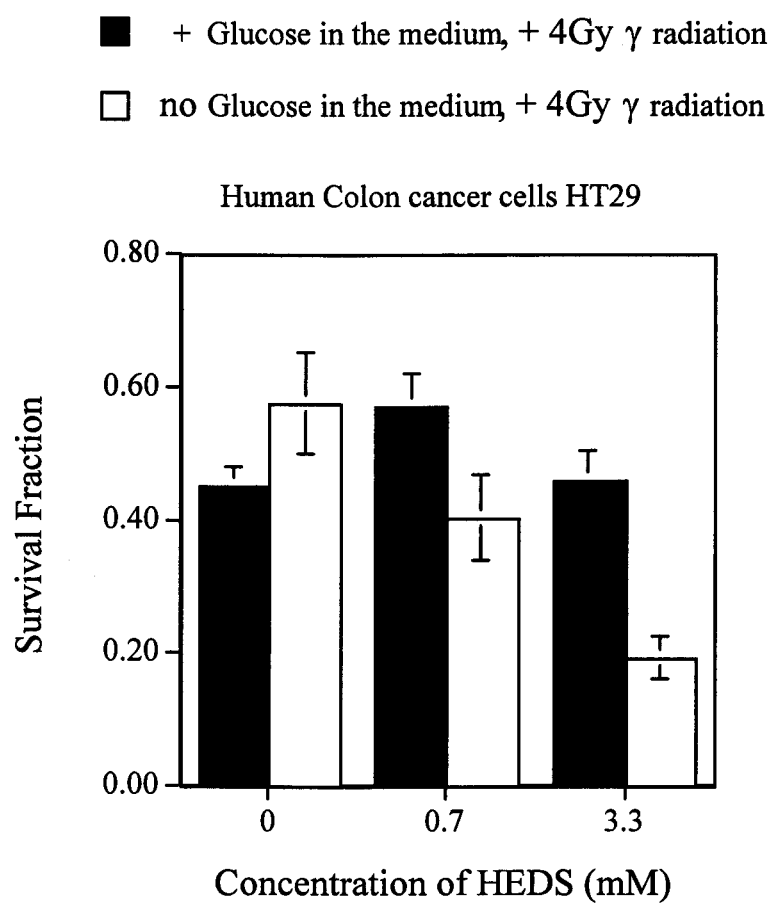
FIG. 4 is a graph depicting the survival of radiation resistant human colon cancer cells exposed to 4Gy γ irradiation in the presence or absence of glucose and various amounts of HEDS.

The lack of detoxification of HEDS by glucose deprived cancer cells is responsible for the better response of human colon cancer cells to radiation shown in FIGS. 2 and 4.

Figure 5:
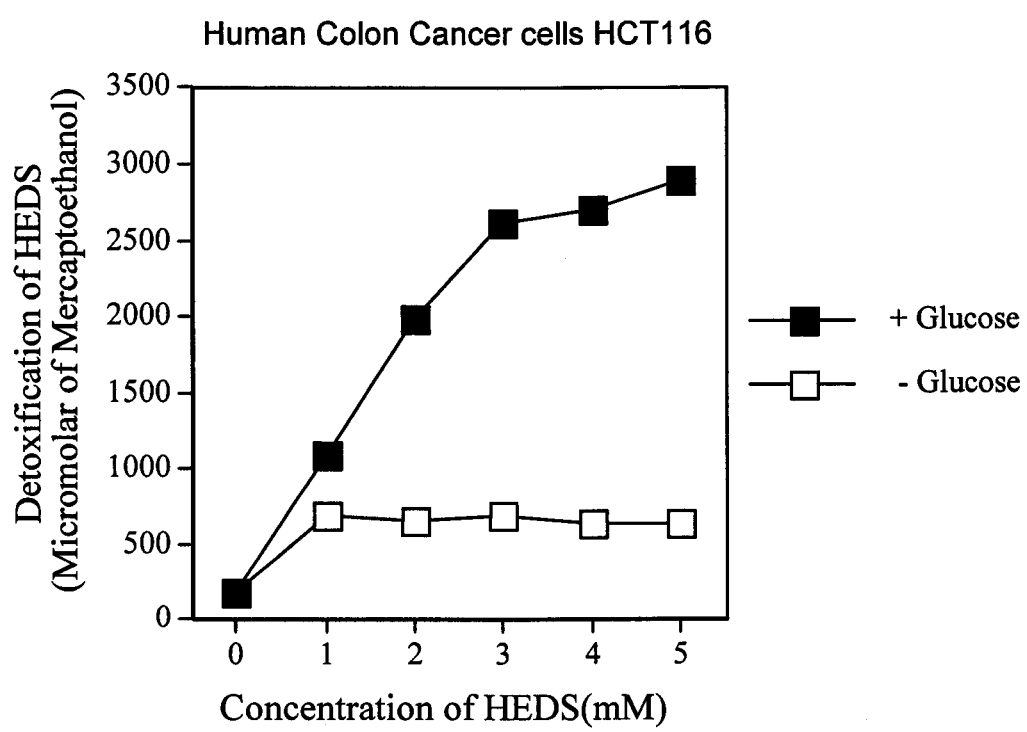
FIG. 5 is a graph providing the amount of mercaptoethanol as a function of HEDS concentration for radiation sensitive human colon cancer cells in the presence or absence of glucose.
Figure 6:
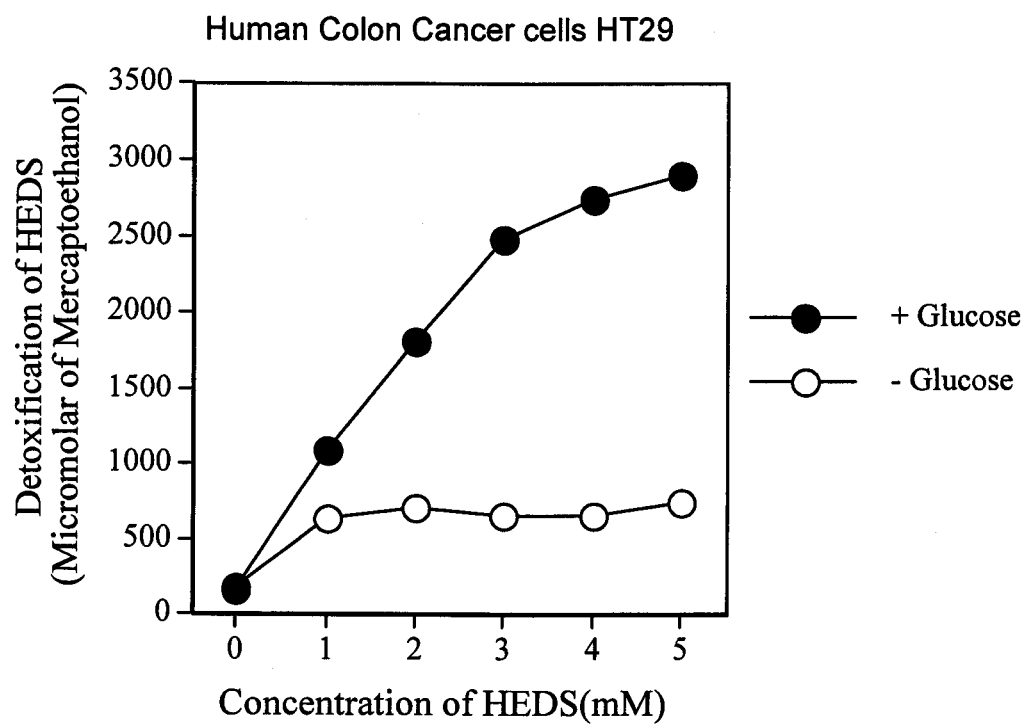
FIG. 6 is a graph providing the amount of mercaptoethanol as a function of HEDS concentration for radiation resistant human colon cancer cells in the presence or absence of glucose.

FIGS. 5 and 6 show that HEDS is not effectively converted into mercaptoethanol (ME), a detoxification process, in glucose deprived human cancer cells. The figures shows that cells incubated with glucose are able to generate up to 3000 μM of non toxic ME. Cells without glucose are six times less efficient in converting HEDS into non toxic ME. Glucose, a substrate required for oxidative pentose phosphate cycle to convert HEDS into ME is necessary for the effective detoxification of HEDS. This phenomenon was observed both in radiation sensitive (HCT116) and resistant (HT29) colon cancer cells.

For FIGS. 5 and 6, the detoxification/bioreduction of HEDS by human colon cancer cells HCT116 and HT29, respectively, was performed by depriving the cells of glucose for 4 hours. The cells were then treated with HEDS for three hours and 0.5 ml of the extracellular medium from the dish was transferred to a microfuge tube containing 0.5 ml of sulphosalicyclic acid (SSA) lysis buffer. The samples were centrifuged at high speed in a Fisher 59A (Pittsburgh, Pa.) microfuge and the supernatant was used for quantification of bioreduction as measured by DTNB reactive mercaptoethanol (ME). Each experiment was repeated at least three times with errors as shown unless smaller than points plotted.

Figure 7:
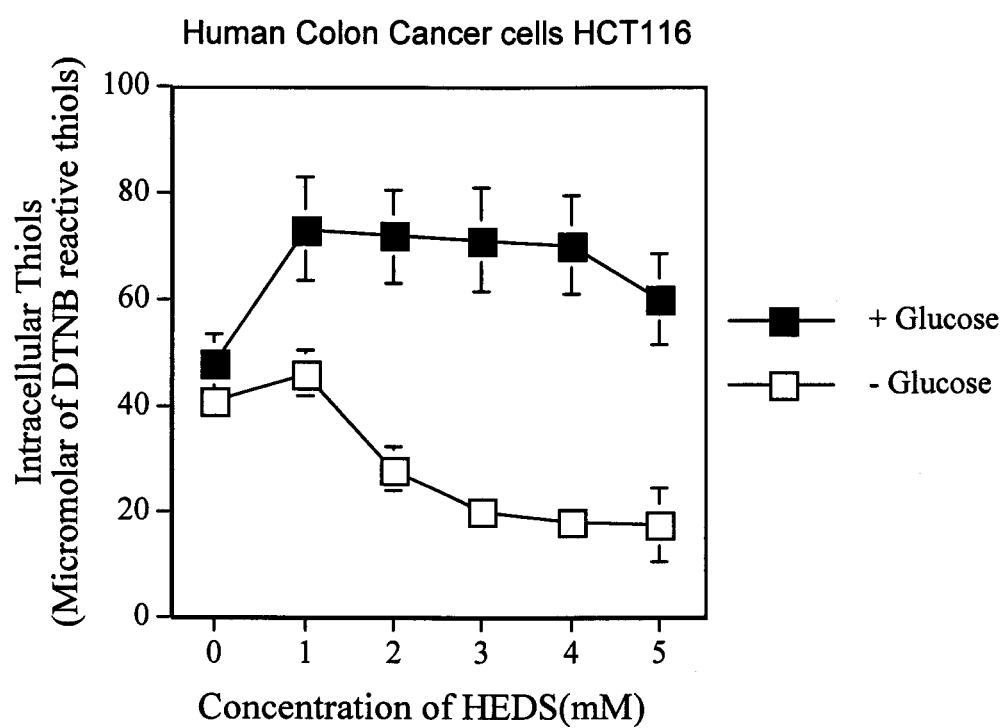
FIG. 7 is a graph depicting the amount of intracellular thiols as a function of HEDS concentration for radiation sensitive human colon cancer cells in the presence or absence of glucose.
Figure 8:
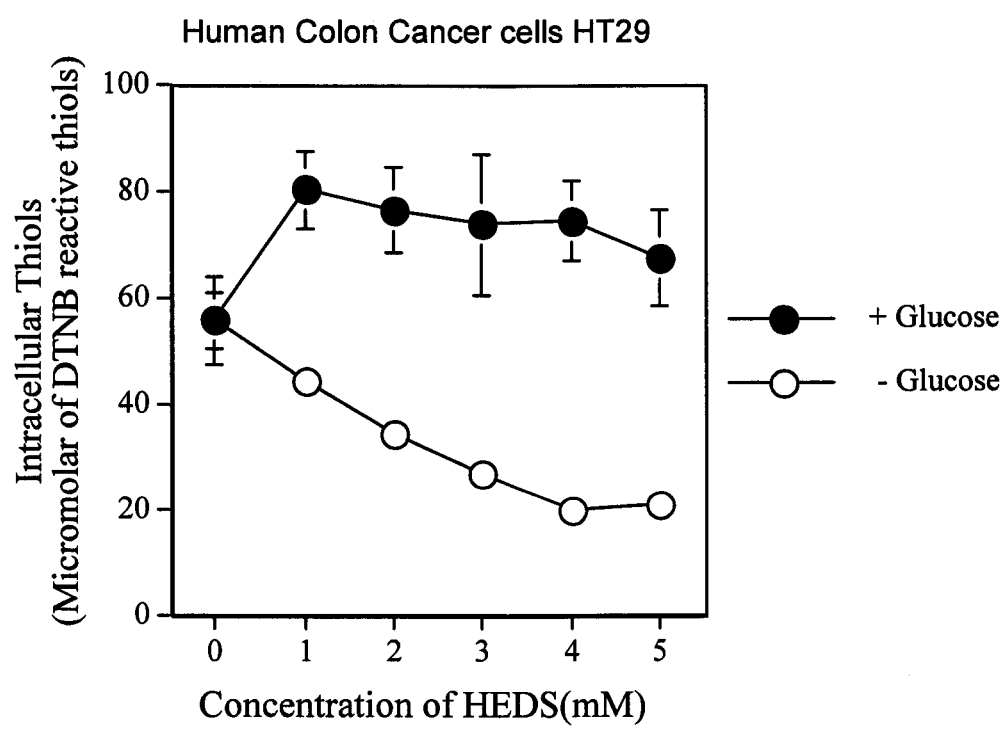
FIG. 8 is a graph depicting the amount of intracellular thiols as a function of HEDS concentration for radiation resistant human colon cancer cells in the presence or absence of glucose.

FIGS. 7 and 8 show that HEDS decreased the intracellular thiols in both radiation sensitive (HCT116) and radiation resistant (HT29) human colon cancer cells only in the absence of glucose. The figures demonstrate that cells with glucose are able to cope up with the treatment of HEDS by maintaining the intracellular thiols. In contrast, the intracellular thiols decreased as low as 40% of the control in glucose deprived cells after HEDS treatment. This phenomenon was observed both in radiation sensitive (HCT116) and resistant (HT29) colon cancer cells.

The depletion of intracellular thiols by HEDS in human colon cancer cells HCT116 and HT29 was determined by first depriving the cells of glucose for 4 hours. After three hours of HEDS treatment, the attached cells were washed with cell rinse and lysed with 1 ml of sulphosalicyclic acid (SSA) lysis buffer. The samples were then centrifuged at high speed in a Fisher 59A microfuge and the supernatant was used for quantification of intracellular thiols using Ellman's reagent. Each experiment was repeated at least three times with errors as shown unless smaller than points plotted.

The results shown in FIGS. 1-8 clearly demonstrate that HEDS improves the response of human cancer cells to DNA damaging agents by altering the thiol status of glucose deprived cancer cells.

EXAMPLE III

Figure 9:
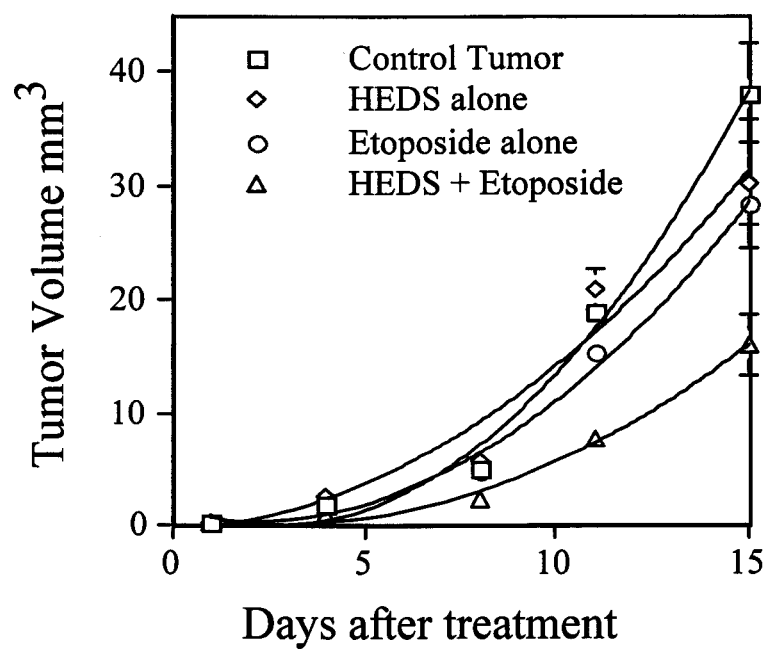
FIG. 9 is a graph of volume of breast tumor xenografts over time in control rats and rats treated with HEDS, etoposide, or HEDS and etoposide.

The use of HEDS, an oxidant/disulfide, to increase the response of tumor xenografts to topoisomerase II inhibitor, etoposide, was also investigated. FIG. 9 demonstrates that HEDS treatment increases the response (at least 50% better response) of tumor xenografts in rats to etoposide, a topoisomerase II inhibitor that also kills cells by inducing DNA damage. The effect of HEDS (0 and 10 mg/kg/day) on the response of tumor to etoposide (12 mg/Kg/day) was determined in rats with tumor of approximately 8×8 mm in size. HEDS in physiological saline was administered at 0 and 10 mg/kg via IP injections. At one hour after HEDS administration, etoposide was administered to these rats by IP. This treatment was continued for three consecutive days. Tumor growth was measured twice a week for up to two weeks. The results suggested that tumors had a 50% better response when treated with HEDS and etoposide as compared to etoposide alone.

Figure 10:
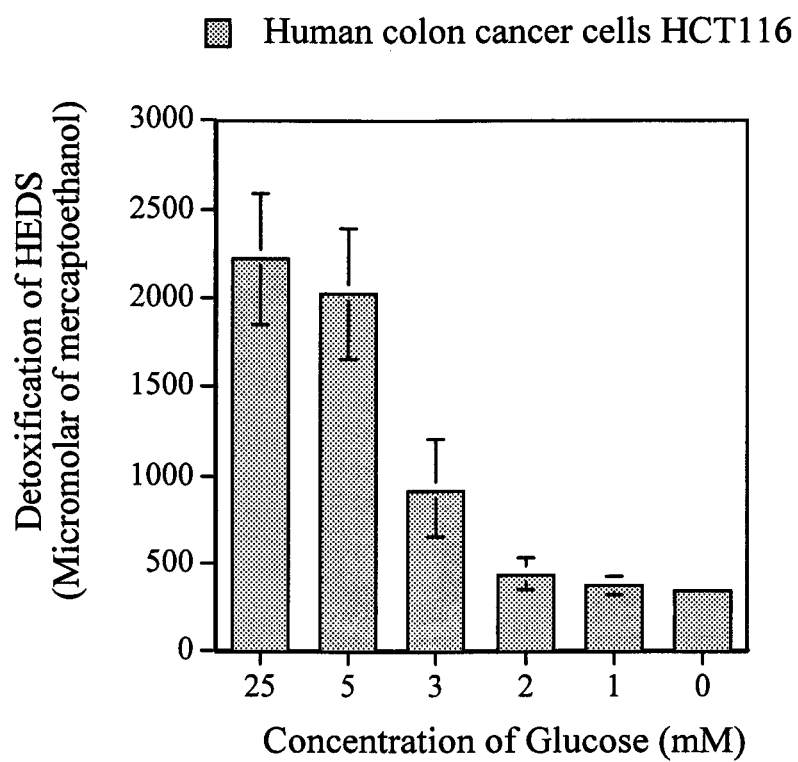
FIG. 10 is a graph of the detoxification of HEDS (based on the concentration of mercaptoethanol) in human colon cancer cells as a function of glucose concentration.
Figure 11:
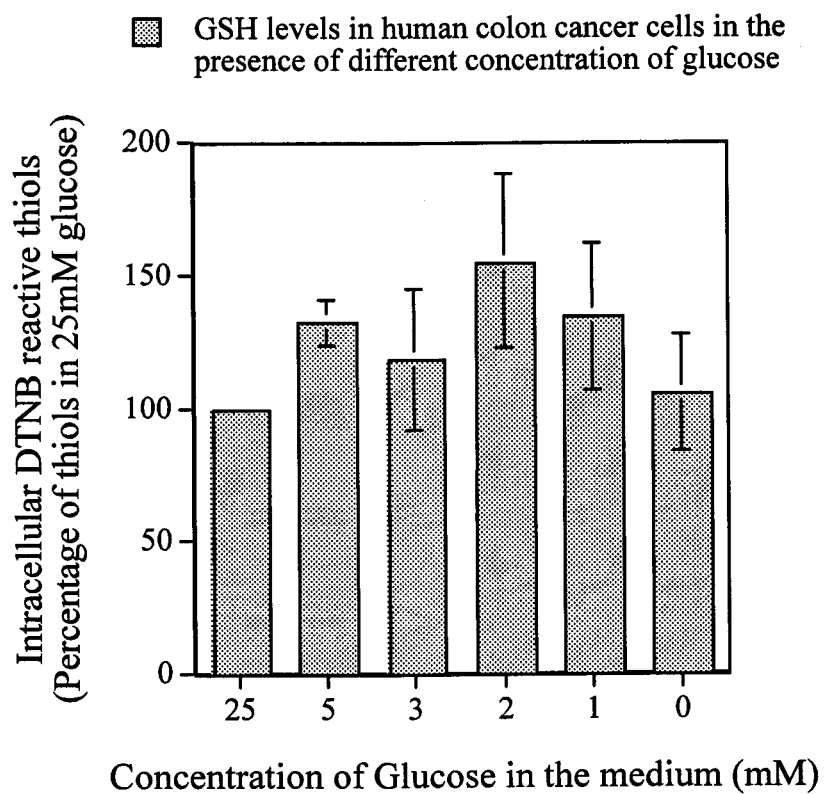
FIG. 11 is a graph depicting the intracellular concentration of thiols in human colon cancer cells at different concentrations of glucose.
Figure 12:
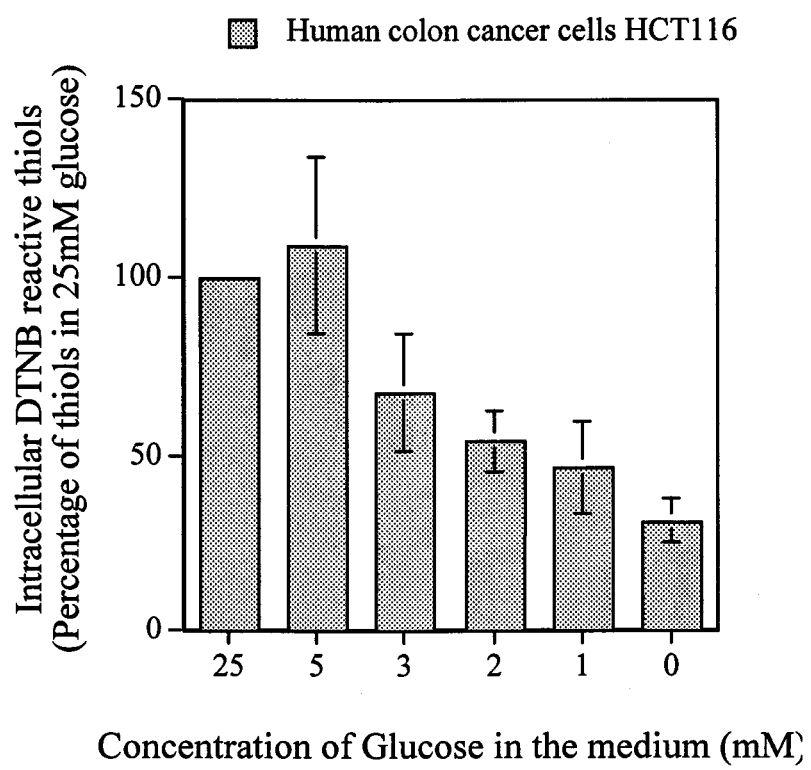
FIG. 12 is a graph showing the intracellular concentration of thiols in human colon cancer cells treated with HEDS and different concentrations of glucose.

This increased response seen with HEDS is consistent with cancer cells not being able to detoxify HEDS effectively in vitro at low concentrations (1-3 mM) of glucose compared to physiological concentrations of glucose (5 mM) resulting in intracellular thiol depletion (see also FIGS. 10-12). These in vitro and in vivo results suggest that physiological concentration (5 mM) of glucose can easily detoxify HEDS (FIGS. 10 and 11), but tumors with less than 3 mM glucose will be affected by HEDS (FIGS. 10 and 12).

For FIG. 10, glucose concentration dependent detoxification/bioreduction of HEDS by human colon cancer cells HCT116 was determined by incubating the cells with different concentrations of glucose for 4 hours. After three hours of HEDS treatment, 0.5 ml of the extracellular medium from the dish was transferred to a microfuge tube containing 0.5 ml of sulphosalicyclic acid (SSA) lysis buffer. The samples were centrifuged at high speed in a Fisher 59A microfuge and the supernatant was used for quantification of bioreduction as measured by DTNB reactive mercaptoethanol (ME). Each experiment was repeated at least three times with errors as shown unless smaller than points plotted.

For the estimation of intracellular thiols in HCT116 cells, the cells were incubated with different concentrations of glucose for 4 hours. For FIG. 12, the cells were then treated with HEDS for 3 hours. After treatment, the attached cells were washed with cell rinse and lysed with 1 ml of sulphosalicyclic acid (SSA) lysis buffer. The samples were centrifuged at high speed in a Fisher 59A microfuge and the supernatant was used for quantification of intracellular thiols using Ellman's reagent. Each experiment was repeated at least three times with errors as shown unless smaller than points plotted.

EXAMPLE IV

In addition to HEDS, MPG disulfide was tested. The structure of MPG disulfide is:

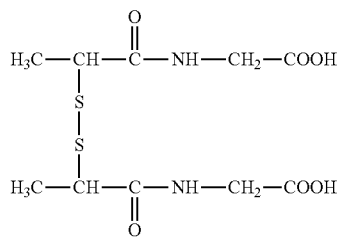 [SMILES: CC(SSC(C)C(=O)NCC(=O)O)C(=O)NCC(=O)O]

This compound was synthesized by Biosynthesis Inc. (Lewisville, Tex.) using the symmetrical disulfide synthesis method. The observed mass (348.21) determined by mass spectroscopy is consistent with the molecular weight of MPG disulfide calculated (324.40) from the chemical structure of MPG disulfide. The purity of the compound is >90% as determined by thin layer chromatography (eluent: n-BuOH:HOAc:$H_2O$ 4:2:1).

The efficacy of MPG disulfide in improving the response to cisplatin in the breast tumor xenograft model in rats was tested. MPG disulfide was tested against two different tumor sizes. These different tumor sizes were achieved by growing the tumor in rats for up to 6 days (small tumor, FIG. 13) or 12 days (large tumor, FIGS. 14 and 15). MPG disulfide was determined to be non-toxic to the animals.

The response of tumors to MPG disulfide was determined in rats with either small tumors (approximately 139 $mm^3$) or large tumors (approximately 2837 $mm^3$). MPG disulfide in physiological saline was administered at 40 mg/Kg/day via IP injections. The control animals were treated with saline. This treatment was continued for three consecutive days. This treatment schedule did not cause any observable side effects in these animals. Each group (control or MPG disulfide) consists of at least three animals. Each data point is mean of at least three animals with standard error as shown unless smaller than points plotted.

The improved response of large tumors to cisplatin by MPG disulfide was determined in rats with tumors of approximately 2837 $mm^3$ in tumor volume. MPG disulfide in physiological saline was administered at 40 mg/kg/day via IP injections. At one hour after MPG disulfide administration, cisplatin (2 mg/kg) was administered to these rats by IP. MPG treatment alone without cisplatin was continued for two more days in these animals. This treatment schedule did not cause any observable side effects in these animals. Each group (cisplatin or MPG disulfide with cisplatin) consists of at least three animals. Each data point is mean of at least three animals with standard error as shown unless smaller than points plotted.

Figure 13:
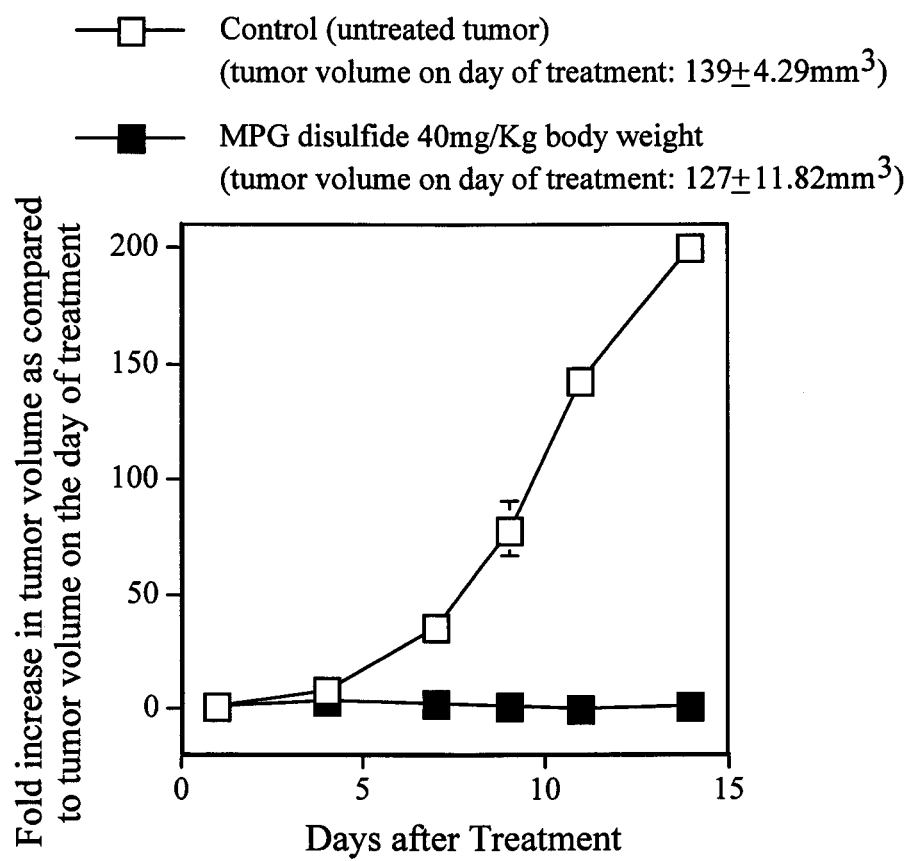
FIG. 13 is a graph of fold increase in tumor volume over time in a breast tumor xenograft rat model. Rats with small tumors (approximately 139 mm$^3$) were either untreated (control) or administered MPG disulfide 40 mg/Kg/day.

All untreated small tumors increased the size by almost 200 fold from 136±4.37 $mm^3$ to 27,300 $mm^3$ in 13 days (FIG. 13). These animals were euthanized at that time. Significantly, MPG disulfide itself completely inhibited the growth of small size tumors from 139±4.29 $mm^3$ on the day of treatment to 126±119 $mm^3$ on day 13 (FIG. 13).

Figure 14:
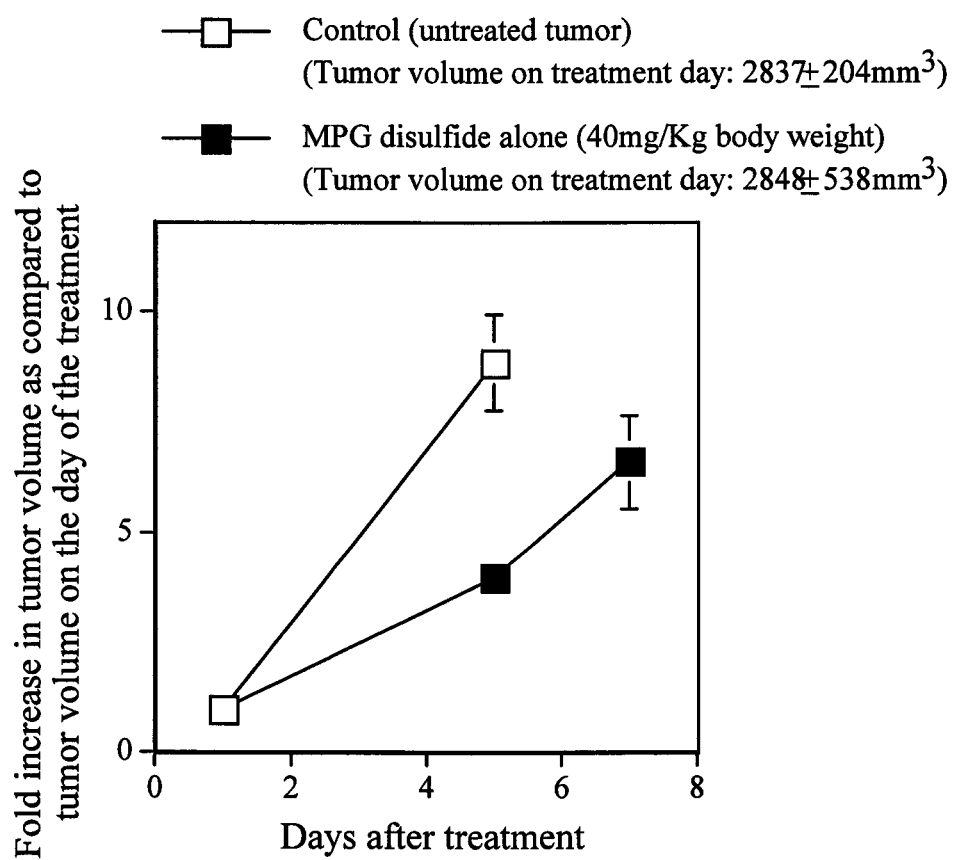
FIG. 14 is a graph of fold increase in tumor volume over time in a breast tumor xenograft rat model. Rats with large tumors (approximately 2837 mm$^3$) were either untreated (control) or administered MPG disulfide 40 mg/Kg/day.

For tumors of larger size, all untreated tumors increased in size by almost tenfold from 2837±204 $mm^3$ to 25,015±2855 $mm^3$ in 5 days (FIG. 14). These animals were euthanized at that time. The growth of MPG disulfide treated tumors was increased only by 3 fold from 2848±538 $mm^3$, which was smaller than the untreated animals by 2.5 fold on day 5 after the treatment (FIG. 14). The tumors continued to grow at the slower rate for up to a maximum size of 18,038±1289 $mm^3$ on day 8.

Figure 15:
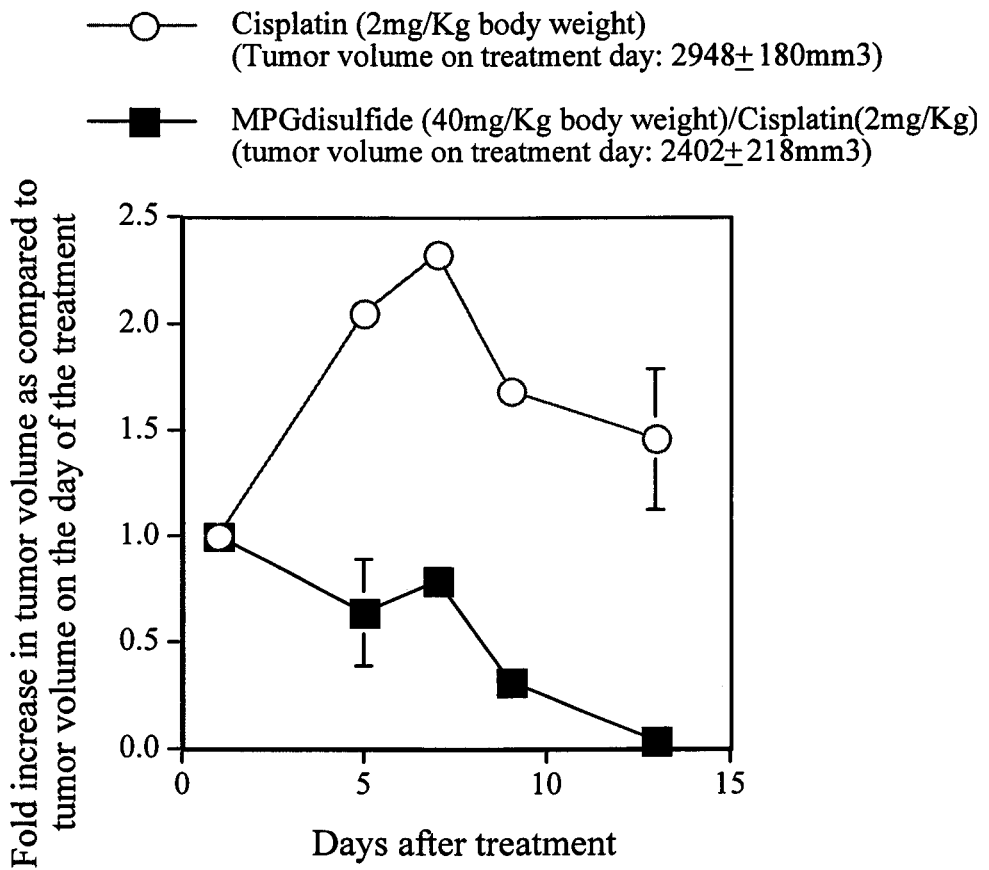
FIG. 15 is a graph of fold change in tumor volume over time in a breast tumor xenograft rat model. Rats with large tumors (approximately 2837 mm$^3$) were treated with cisplatin (2 mg/Kg body weight) with or without MPG disulfide 40 mg/Kg/day.
Figure 17:
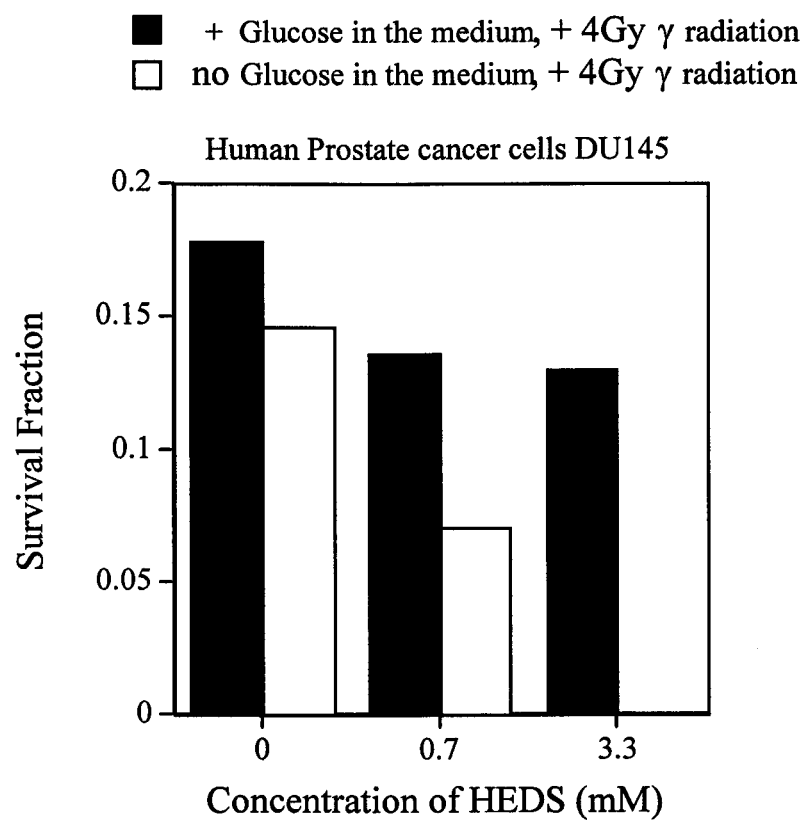
FIG. 17 is a graph depicting the survival of human prostate cancer cells exposed to 4Gy γ irradiation in the presence or absence of glucose and various amounts of HEDS.

Cisplatin alone inhibited tumor growth from 2948±180 $mm^3$ to 4355±577 $mm^3$ on day 13 after the treatment (FIG. 17). However, cisplatin and MPG disulfide combinations decreased the tumor size significantly better (38 fold smaller compared to cisplatin group) than either treatment alone with tumor volume decreasing from 2402±218 $mm^3$ to 112±47 $mm^3$ on day 13 after the start of the treatment (FIG. 15).

These results demonstrated that MPG disulfide acts as a chemotherapeutic agent on tumors even when administered alone, particularly small tumors (less than about 500 $mm^3$). However, MPG disulfide in combination with a chemotherapeutic agent, such as cisplatin, completely eliminated tumors, even large tumors, where cisplatin alone did not.

EXAMPLE V

Figure 16:
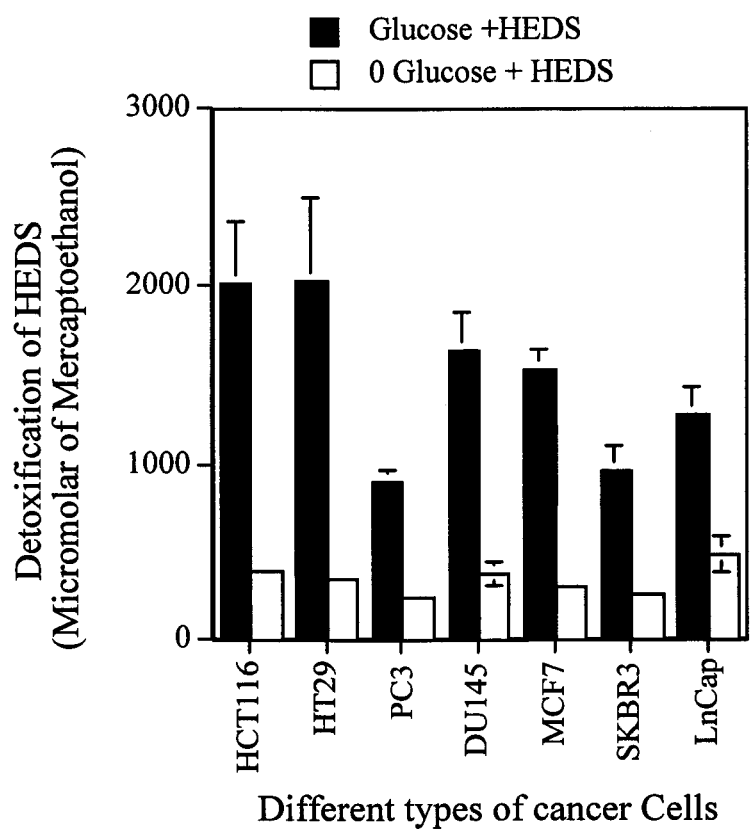
FIG. 16 is a graph the detoxification of HEDS (based on the concentration of mercaptoethanol) in various cancer cells either in the presence or absence of glucose.

In addition to human colon cancer cells (HCT116 and HT29; see Example II), disulfide containing compounds were also tested against other human cancer cells in vitro including breast and prostate cancer cells. As observed with the two human colon cancer cell lines, the two human breast cancer cell lines (MCF7, SKBR3) and four prostate cancer cell lines (DU145, PC3, DU145, LnCaP) also demonstrated an inability to convert HEDS into ME, a detoxification process, in glucose depleted medium. FIG. 16 demonstrates that six different types of human cancer cells (HCT116, HT29, PC3, DU145, MCF7, SKBR3, LnCaP) lack the ability to convert HEDS into ME in the absence of glucose (mean and standard error of three experiments are presented). These results indicate that the administration of a disulfide compound, such as HEDS and/or MPG disulfide, can be used to treat a wide variety of cancers, particularly when used in combination with other conventional cancer therapies.

Figure 18:
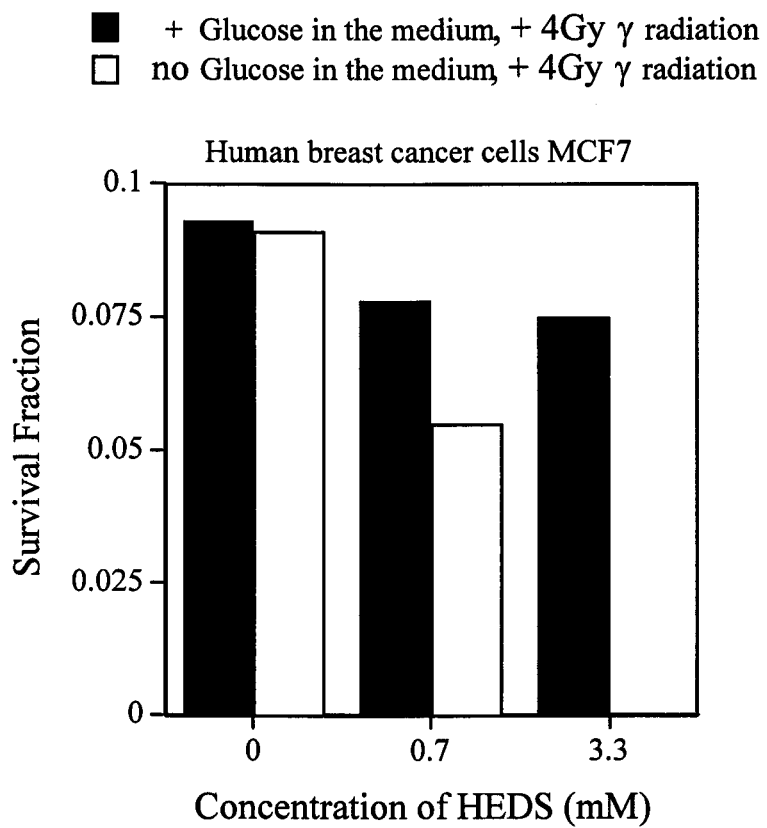
FIG. 18 is a graph depicting the survival of human breast cancer cells exposed to 4Gy γ irradiation in the presence or absence of glucose and various amounts of HEDS.

FIGS. 17 and 18 demonstrate that the administration of HEDS also enhances the response of other types of cancer cells to chemotherapeutic agents, particularly DNA damaging agents. FIGS. 17 and 18 show the impact of HEDS on the radiation response of a breast cancer cell line (MCF7) and a prostate cancer cell line (DU145) in the presence and absence of glucose. The results demonstrate that the radiation responses of both MCF7 and DU145 were significantly increased by HEDS in the absence of glucose. These results with radiation indicate that disulfide containing compounds could be universally used to increase the response of cancer cells to chemotherapeutic agents, particularly DNA damaging agents.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising at least one disulfide containing compound, at least one chemotherapeutic agent, and at least one pharmaceutically acceptable carrier, wherein said disulfide containing compound comprises a first lower alkyl linked by at least one disulfide bond to a second lower alkyl,
wherein said first and second lower alkyls each comprise 1 to 5 carbons, and
wherein said disulfide containing compound is selected from the group consisting of hydroxyethyldisulfide (HEDS), disulfide of mercaptoethanol (ME) and 2-sulfanylethanesulfonate (mesna), and a disulfide containing compound wherein said first lower alkyl is mercaptopropionylglycine (MPG).

2. The composition of claim 1, further comprising at least one inhibitor of glucose-6-phosphate dehydrogenase (G6PD).

3. The composition of claim 1, wherein said disulfide containing compound is disulfide of mercaptopropionylglycine (MPG).

4. The composition of claim 1, wherein said disulfide containing compound is selected from the group consisting of hydroxyethyldisulfide (HEDS), disulfide of mercaptopropionylglycine (MPG), disulfide of MPG and ME, disulfide of MPG and mesna, and disulfide of ME and mesna.

5. The composition of claim 1, wherein said chemotherapeutic agent is selected from the group consisting of a topoisomerase II inhibitor and a platinum complex.

6. The composition of claim 2, wherein said inhibitor of G6PD is selected from the group consisting of dehydroepiandrosterone (DHEA), DHEA-sulfate, 2-deoxyglucose, halogenated DHEA, epiandrosterone, isoflurane, sevoflurane, diazepam, and G6PD siRNA molecules.

7. A composition comprising at least one disulfide containing compound, at least one hypoxic toxin, and at least one pharmaceutically acceptable carrier, wherein said disulfide containing compound comprises a first lower alkyl linked by at least one disulfide bond to a second lower alkyl,
wherein said first and second lower alkyls each comprise 1 to 5 carbons, and
wherein said disulfide containing compound is selected from the group consisting of hydroxyethyldisulfide (HEDS), a disulfide of mercaptoethanol (ME) and 2-sulfanylethanesulfonate (mesna), and a disulfide containing compound wherein said first lower alkyl is mercaptopropionylglycine (MPG).

8. The composition of claim 7, wherein said disulfide containing compound is disulfide of mercaptopropionylglycine (MPG).

9. The composition of claim 7, wherein said hypoxic toxin is selected from the group consisting of tirapazamine, AQ4N, 5-nitroimidazole, nimorazole, etanidazole, mitomycin C analog E09, 2-nitroimidazole CI-1010, and other hypoxic specific bioreductive drugs.

10. The composition of claim 7, further comprising at least one chemotherapeutic agent.

* * * * *